(12) United States Patent
Gurewitsch (10) Patent No.: US 6,400,988 B1
(45) Date of Patent: Jun. 4, 2002

(54) IMPLANTABLE CARDIAC DEVICE HAVING PRECISION RRT INDICATION

(75) Inventor: Reinaldo Gurewitsch, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/507,023

(22) Filed: Feb. 18, 2000

(51) Int. Cl.[7] .............................................. A61N 1/378
(52) U.S. Cl. ...................................................... 607/29
(58) Field of Search ................................. 607/5, 9, 29

(56) References Cited

U.S. PATENT DOCUMENTS

| | | | |
|---|---|---|---|
| 4,290,429 A | 9/1981 | Blaser .......................... 128/419 |
| 4,556,061 A | 12/1985 | Barreras et al. ............... 607/32 |
| 4,712,555 A | 12/1987 | Thornander et al. ......... 128/419 |
| 4,715,381 A | 12/1987 | Moberg ........................ 607/29 |
| 4,788,980 A | 12/1988 | Mann et al. ................. 128/419 |
| 4,940,052 A | 7/1990 | Mann et al. ................. 128/419 |
| 4,944,298 A | 7/1990 | Sholder ....................... 128/419 |
| 5,092,330 A | 3/1992 | Duggan ....................... 128/630 |
| 5,193,538 A | 3/1993 | Ekwall ........................ 128/419 |
| 5,325,041 A | 6/1994 | Briggs .......................... 320/44 |
| 5,336,242 A | 8/1994 | Zadeh ......................... 607/11 |
| 5,458,624 A | 10/1995 | Renirie et al. ................ 607/29 |
| 5,496,353 A | 3/1996 | Grandjean et al. ............ 607/29 |
| 5,507,786 A | 4/1996 | Morgan et al. ............... 607/27 |
| 5,620,474 A | 4/1997 | Koopman .................... 607/29 |
| 5,722,999 A | 3/1998 | Snell ............................ 607/32 |
| 5,741,307 A | 4/1998 | Kroll ............................. 607/5 |
| 5,769,873 A | 6/1998 | Zadeh ........................ 607/229 |
| 5,800,472 A * | 9/1998 | Mann .......................... 607/29 |
| 6,108,579 A * | 8/2000 | Snell et al. ................... 607/29 |
| 6,167,309 A * | 12/2000 | Lyden .......................... 607/29 |
| 6,185,461 B1 * | 2/2001 | Er ............................... 607/27 |

* cited by examiner

Primary Examiner—Carl Layno (57) ABSTRACT

An implantable cardiac device including a depletable power source, having an initial energy capacity, and method provide precise recommended replacement time and end of life indications for the depletable power source. The recommended replacement times and end of life times are based upon the actual remaining energy of the depletable power source. The recommended replacement time and end of life time are stored in memory for later transmission by a telemetry circuit to a nonimplantable receiver for read out or display.

51 Claims, 3 Drawing Sheets

IMPLANTABLE CARDIAC DEVICE HAVING PRECISION RRT INDICATION

FIELD OF THE INVENTION

The present invention is generally directed to an implantable cardiac device which is powered by a depletable power source. The present invention is more particularly directed to such a device which provides precise recommended replacement time and absolute replacement time (sometimes referred to as "end-of-life") indications based upon actual remaining energy capacity of the depletable power source.

BACKGROUND OF THE INVENTION

Implantable cardiac devices are well known in the art. Such devices include implantable monitors which monitor heart activity over extended periods of time for diagnostic purposes, implantable pacemakers which both monitor heart activity and apply stimulation pulses to a heart when required to maintain normal sinus rhythm, and implantable cardioverter-defibrillators which monitor heart activity for tachyarrhythmias and apply shocking stimulation pulses to a heart to return the heart to normal sinus rhythm. Implantable cardioverter-defibrillators also commonly include pacemaker functionality.

Since implantable cardiac devices are implanted beneath the skin of a patient, they are powered by a depletable power source, such as a battery. When the remaining battery energy capacity falls below a certain lower limit corresponding to an absolute replacement time, sometimes referred to as "end-of-life" (EOL), the device must be replaced. Further, prior to EOL, as for example 90 days prior to EOL, the battery will reach a remaining energy capacity corresponding to the recommended replacement time (RRT). An RRT indication is generally provided to alert the patient's physician that EOL is imminent and is timed relative to EOL to afford the physician sufficient time to schedule replacement of the device before EOL is reached.

Most present RRT and EOL indicators utilize battery voltage and/or impedance and their correlation to the remaining battery capacity to provide information as to when RRT and EOL will be reached. Unfortunately, the tolerances in the battery voltage measurements as well as battery impedance have too wide a variance to provide an adequate time margin for replacement after an indication of RRT. Many implantable devices are thus explanted based upon these inadequate measurements. These indicators generally start providing remaining battery capacity information only during the final 20 percent of battery life because significant changes in these factors do not occur during the initial 80 percent of the battery life. This has resulted in conflicting RRT indications in the field.

Further, in some instances, follow-up times may be relatively long. This can result in an implantable cardiac device entering not only RRT but also even EOL without clinical assistance.

SUMMARY OF THE INVENTION

The present invention provides an implantable cardiac device and method which monitors actual remaining depletable power source energy capacity for making accurate RRT and/or EOL indications. The amount of current provided by the power source is constantly measured by a current monitor to derive a first average of current, provided by the power source since its initial hook-up or "beginning-of-life" (BOL), and a second average current, provided over a last 24 hour period.

The remaining energy capacity of the power source is determined by multiplying the first average current by the time since BOL to derive actual used capacity and then subtracting the actual used capacity from the initial capacity of the power source. An EOL date is then calculated by dividing the remaining energy capacity by the second current average to derive the remaining power source life and then adding the remaining power source life to a current date. The RRT date may then be determined by subtracting a fixed time period, such as 90 days, for example, from the EOL date.

The RRT and EOL dates provided are extremely accurate because they are based upon the actual remaining power source energy capacity. Further, a first alarm may be issued when the current date equals or exceeds the RRT date and a second alarm may be issued when the current date equals or exceeds the EOL date.

BRIEF DESCRIPTION OF THE DRAWINGS

The above and other aspects, features and advantages of the present invention will be apparent from the following more particular description thereof, presented in conjunction with the accompanying drawings wherein.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention may be used with various types of implantable cardiac devices, including an implantable heart monitor, an implantable pacemaker configured to treat bradycardia and/or tachycardia, an implantable cardioverter/defibrillator (ICD), or a combined ICD and pacemaker.

To better understand the invention, it will first be helpful to have an understanding of the basic functions performed by an implantable cardiac device with which the invention may be used, e.g., an ICD device and/or a dual-chamber pacemaker. While a dual-chamber device has been chosen, this is for teaching purposes only. It is recognized that the present invention could be implemented in a single-chamber device, that one of skill in the art could readily adapt the dual-chamber device shown in FIG. 2 to perform single-chamber functionality, and that a single-chamber device is within the spirit of the invention.

Figure 1:
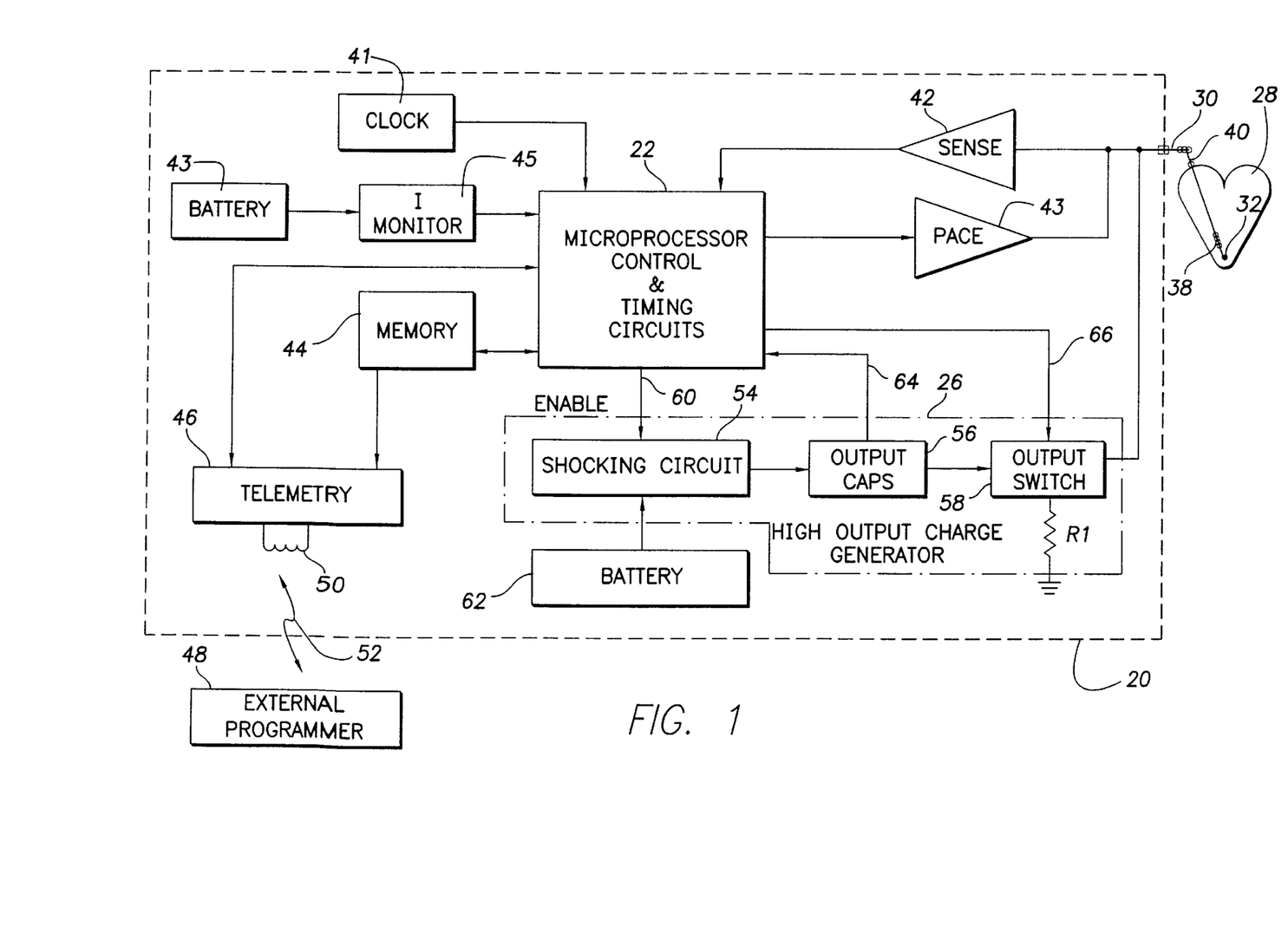
FIG. 1 shows a simplified functional block diagram of an implantable cardioverter/defibrillator (ICD), which represents one type of implantable cardiac stimulation device with which the present invention may be used.
Figure 2:
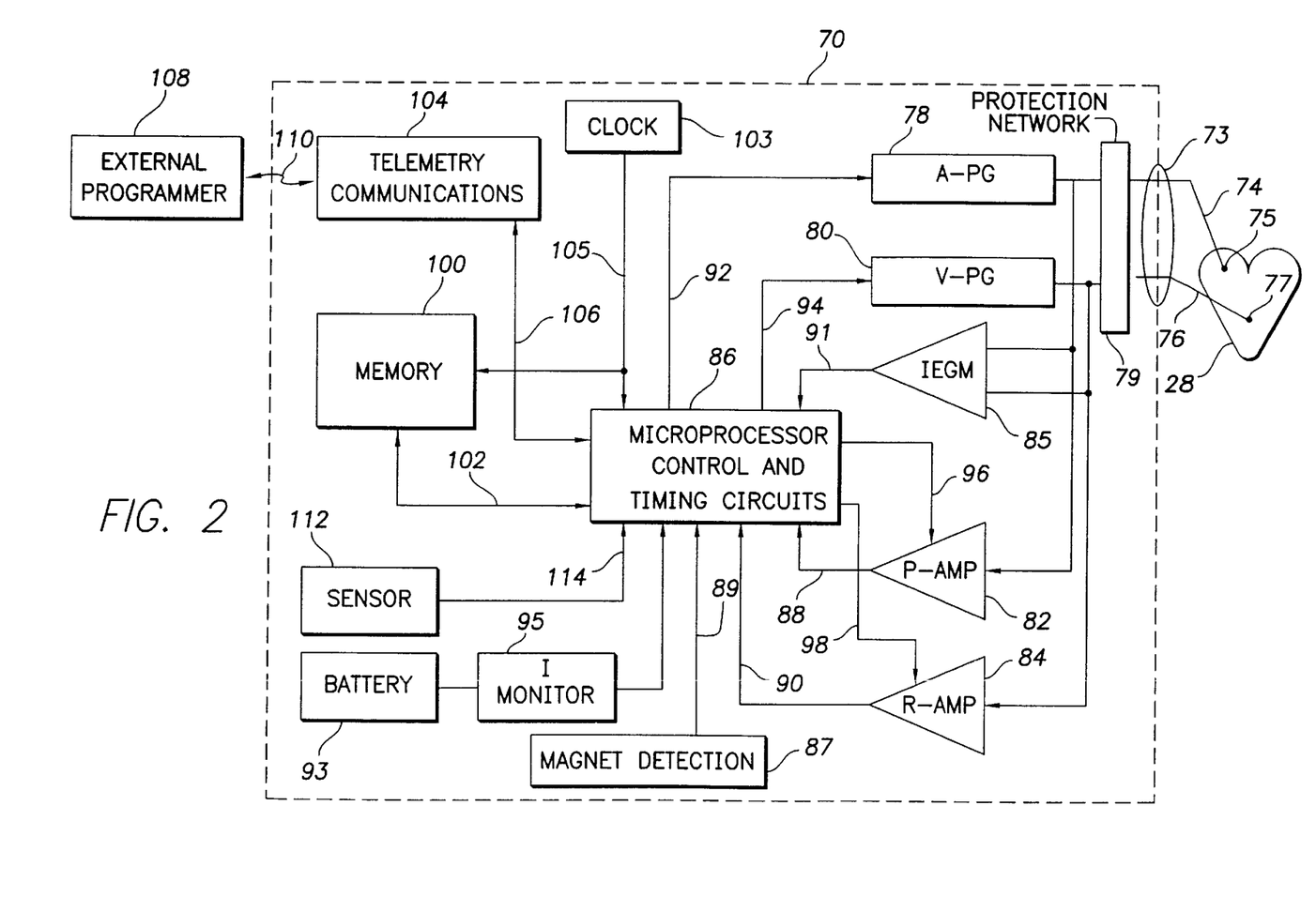
FIG. 2 shows a functional block diagram of an implantable dual-chamber pacemaker, which represents another type of implantable medical device with which the invention may be used.

In FIG. 1, there is shown a simplified functional block diagram of an ICD device 20, and in FIG. 2, there is shown a simplified functional block diagram of a dual-chamber pacemaker 70. It should also be noted that in some instances the functions of an ICD and a pacemaker may be combined within the same stimulation device. However, for teaching purposes, the devices will be described as separate stimulation devices.

It is the primary function of an ICD device to sense the occurrence of an arrhythmia, and to automatically apply an appropriate electrical shock therapy to the heart aimed at terminating the arrhythmia. To this end, the ICD device 20 as shown in the functional block diagram of FIG. 1, includes a control and timing circuit 22, such as a microprocessor, state machine or other such control circuitry, that controls a high output charge generator 26. The high output charge generator 26 generates electrical stimulation pulses of moderate or high energy (corresponding to cardioversion or defibrillation pulses, respectively), e.g., electrical pulses having energies of from 1–10 joules (moderate), or 11–40 joules (high), as controlled by the control/timing circuit 22.

Such moderate or high energy pulses are applied to the patient's heart through at least one lead 30 having at least two defibrillation electrodes, such as coil electrodes 38 and 40. The lead 30 preferably also includes at least one electrode for pacing and sensing functions, such as electrode 32. Typically, the lead 30 is transvenously inserted into the heart so as to place the coil electrodes 38 and 40 in the apex of the heart and in the superior vena cava, respectively. While only one lead is shown in FIG. 1, it is to be understood that additional defibrillation leads and electrodes may be used as desired or needed in order to efficiently and effectively apply the shock treatment generated by the high voltage generator 26 to the patient's heart 28.

The ICD 20 also includes a sense amplifier 42 that is coupled to at least one sensing electrode 32. It is the function of the sense amplifier 42 to sense the electrical activity of the heart 28, as is known in the art, to generate an electrogram including R-waves which occur upon depolarization, and hence contraction, of ventricular tissue; and P-waves which occur upon the depolarization, and hence contraction, of atrial tissue. Thus by sensing R-waves and/or P-waves through the sense amplifier 42, and by providing the control/timing circuit 22 with the generated electrogram, the control/timing circuit 22 is able to make a determination as to the rate and regularity of the patient's heartbeat. Such information, in turn, allows the control/timing circuit 22 to determine whether the heart 28 of a patient is experiencing an arrhythmia, and to apply appropriate stimulation therapy.

The control/timing circuit 22 further has a memory circuit 44 coupled thereto wherein the operating parameters used by the control/timing circuit 22 are stored. Such operating parameters define, for example, the amplitude of each shock energy pulse to be delivered to the patient's heart 28 within each tier of therapy, as well as the duration of these shock pulses. The memory 44 may take many forms, and may be subdivided into as many different memory blocks or sections (addresses) as needed to store desired data such as RRT and/or EOL times and control information.

Advantageously, the operating parameters of the implantable device 20 may be non-invasively programmed into the memory 44 through a telemetry circuit 46, in telecommunicative contact with an external programmer 48 by way of a suitable coupling coil 50. The coupling coil may serve as an antenna for establishing a radio frequency (RF) communication link 52 with the external programmer 48; or the coil 50 may serve as a means for inductively coupling data to and from the telemetry circuit 46 from and to the external programmer 48, as is known in the art. Further, such telemetry circuit 46 advantageously allows status information relating to the operation of the ICD 20 as contained in the control/timing circuit 22 or memory 44, such as RRT and/or EOL times determined in accordance with the present invention to be sent to the external programmer 48 through the established link 52.

The control/timing circuit 22 includes appropriate processing and logic circuits for analyzing the electrogram generated by the sense amplifier 42 and determining if such signals indicate the presence of an arrhythmia. Typically, the control/timing circuit 22 is based on a microprocessor, or similar processing circuit, which includes the ability to process or monitor input signals (data) in a prescribed manner, e.g., as controlled by program code stored in a designated area or block of the memory 44. The details of the design and operation of the control/timing circuit 22 are not critical to the present invention. Rather, any suitable control/timing circuit 22 may be used that carries out the functions described herein. The use, design, and operation of microprocessor-based control circuits to perform timing and data analyses functions is known in the art.

The ICD 20 further includes a depletable power source or battery 43. The battery provides operating power to all of the circuits of the ICD. Coupled to the battery 43 is a current monitor 45. The current monitor, in accordance with the present invention, continuously senses the total current drawn from the battery 43 by the circuits of the ICD 20. The monitor 45 may include, for example, a resistance which provides a voltage drop proportional to the used current. The voltage drop may then be applied to an analog-to-digital converter to provide a digital representation of the used current to the control circuit 22. As will be seen subsequently, the processor 22 uses the current measurement to determine a first average current which is the average current used since BOL and a second average current which is the average current used over a last 24 hour period.

In FIG. 2, a simplified block diagram of the circuitry needed for a dual-chamber pacemaker 70 is illustrated. The pacemaker 70 is coupled to a heart 28 by way of leads 74 and 76, the lead 74 having an electrode 75 that is in contact with one of the atria of the heart, and the lead 76 having an electrode 77 that is in contact with one of the ventricles of the heart. The leads 74 and 76 are electrically and physically connected to the pacemaker 70 through a connector 73 that forms an integral part of the housing wherein the circuits of the pacemaker are housed.

The connector 73 is electrically connected to a protection network 79, which network 79 electrically protects the circuits within the pacemaker 70 from excessive shocks or voltages that could appear on the electrodes 75 and/or 77 in the event such electrodes were to come in contact with the high voltage signal, e.g., from a defibrillation shock.

The leads 74 and 76 carry stimulation pulses to electrodes 75 and 77 from an atrial pulse generator (A-PG) 78 and a ventricular pulse generator (V-PG) 80, respectively. Further, electrical signals from the atria are carried from the electrode 75 through the lead 74, to the input terminal of an atrial channel sense amplifier (P-AMP) 82; and electrical signals from the ventricles are carried from the electrode 77 through the lead 76, to the input terminal of a ventricular channel sense amplifier (R-AMP) 84. Similarly, electrical signals from both the atria and ventricles are applied to the inputs of an IEGM (intracardiac electrogram) amplifier 85. The amplifier 85 is typically configured to detect an evoked response from the heart 28 in response to an applied stimulus, thereby aiding in the detection of "capture."

The dual-chamber pacemaker 70 is controlled by a control system 86 that typically includes a microprocessor programmed to carry out control and timing functions. The control system 86 receives the atrial electrogram signal from the atrial amplifier 82 over signal line 88. Similarly, the control system 86 receives the ventricular electrogram signal from the ventricular amplifier 84 over signal line 90, and the output signals from the IEGM amplifier 85 over signal line 91. The control system 86 also generates trigger signals that are sent to the atrial pulse generator 78 and the ventricular pulse generator 80 over signal lines 92 and 94, respectively. These trigger signals are generated each time that a stimulation pulse is to be generated by the respective pulse generator 78 or 80. The atrial trigger signal is referred to simply as the "A-trigger" and the ventricular trigger signal is referred to as the "v-trigger."

As shown in FIG. 2, the pacemaker 70 further includes a memory circuit 100 that is coupled to the control system 86 over a suitable data/address bus 102. This memory circuit 100 allows certain control parameters, used by the control system 86 in controlling the operation of the pacemaker, to be programmably stored and modified, as required, in order to customize the pacemaker's operation to suit the needs of a particular patient. Further, data sensed during the operation of the pacemaker may be stored in the memory 100 for later retrieval and analysis. That data may include RRT and/or EOL times as determined in accordance with the present invention.

As with the memory 44 of the ICD device 20 shown in FIG. 1, the memory 100 of the pacemaker 70 (FIG. 2) may take many forms, and may be subdivided into as many different memory blocks or sections (addresses) as needed in order to allow desired data and control information to be stored. Preferably, the memory 100 is capable of storing a relatively large amount of sensed data as a data record, which data record may then be used to guide the operation of the device. That is, the operating mode of the pacemaker may be made dependent, at least in part, on past performance data. For example, an average atrial rate may be determined based on the sensed atrial rate over a prescribed period of time. This average rate may then be stored and updated at regular intervals. Such stored rate may then be compared to a present atrial rate and, depending upon the difference, used to control the operating mode of the pacemaker. Other parameters, of course, in addition to (or in lieu on atrial rate, may be similarly sensed, stored, averaged (or otherwise processed), and then used for comparison purposes against one or more currently sensed parameters. Advantageously, modem memory devices allow for the storage of large amounts of data in this manner.

A clock circuit 103 directs an appropriate clock signal to the control system 86, as well as to any other needed circuits throughout the pacemaker 70 e.g., to the memory 100, by way of clock bus 105.

A telemetry/communications circuit 104 is further included in the pacemaker 70. This telemetry circuit 104 is connected to the control system 86 by way of a suitable command/data bus 106. In turn, the telemetry circuit 104, which is included within the implantable pacemaker 70 may be selectively coupled to an external programming device 108 by means of an appropriate communication link 110, which communication link 110 may be any suitable electromagnetic link, such as an RF (radio frequency) channel, a magnetic link, an optical link, and the like. Advantageously, through the external program 108 and the communication link 110, desired commands may be sent to the control system 86. Similarly, through this communication link 110 with the programmer 108 data commands, either held within the control system 86, as in a data latch, or stored within the memory 100, may be remotely received from the programmer 108. Similarly, data initially sensed through the lead 74 or 76 and processed by the microprocessor control circuits 86, or other data measured within or by the pacemaker 70, such as RRT and/or EOL times may be stored and uploaded to the programmer 108. In this manner, non-invasive communications can be established with the implanted pacemaker from a remote, non-implanted location.

The pacemaker 70 additionally includes a depletable power source such as a battery 93. The battery 93 provides operating power to all of the circuits of the pacemaker 70. The battery 93 is coupled to a current monitor 95. The current monitor may be identical to the current monitor 45 of FIG. 1. Responsive to the digital representation of the used current, the processor 86 determines the first and second average currents as previously described.

It is noted that the pacemaker 70 in FIG. 2 is referred to as a dual-chamber pacemaker because it interfaces with both the atria and the ventricles of the heart. Those portions of the pacemaker 70 that interface with the atria, e.g., the lead 74, the atrial pulse generator 78, and corresponding portions of the control system 86, are commonly referred to as the "atrial channel." Similarly, those portions of the pacemaker 70 that interface with the ventricles, e.g., the lead 76, the ventricular sense amplifier 84, the ventricular pulse generator 80, and corresponding portions of the control system 86, are commonly referred to as the "ventricular channel."

As needed for certain applications, the pacemaker 70 may further include at least one sensor 112 that is connected to the control system 86 of the pacemaker 70 over a suitable connection line 114. A common type of sensor is an activity sensor, such as piezoelectric crystal, that is mounted to the case of the pacemaker. Other types of sensors are also known, such as sensors that sense the oxygen content of blood, respiration rate, pH of blood, body motion, and the like. The type of sensor used is not critical to the present invention. The pacemaker 70 further includes magnet detection circuitry 87, coupled to the control system 86 over signal line 89, as is well known in the art.

As with the ICD device 20 of FIG. 1, the telemetry or communications circuit 104 may be of conventional design. Similarly, the external programmer 108 may be of any suitable design in the art. Likewise, the memory circuit 100 and the circuits utilized in the atrial and ventricular channels may all be of common design as is known in the pacing art. The present invention is not concerned with the details of the circuitry utilized for each of these pacing elements. Rather, it is concerned with the manner in which all of these pacing elements cooperate with each other in order to provide a particular pacing mode of operation. Such cooperation is controlled by the control system 86.

The control system 86 may be realized using a variety of different techniques and/or circuits. The preferred type of control system 86 is a microprocessor-based control system. It is noted, however, that the control system 86 could also be realized using a state machine. Indeed, any type of control circuit or system could be employed for the control system 86. The present invention is likewise not concerned with the details of the control systems 22 and 86. Rather it is concerned with the end result achieved by the control system. That is, so long as the control system 86 controls the operation of the pacemaker (or other medical device)so that the desired functions are achieved as set forth herein, e.g., by following the steps described below in the flow chart of FIG. 3, it matters little what type of control system is used. Those of skill in the implantable medical device art, given the teachings presented herein, should thus be able to fashion numerous different types of control systems or circuits that achieve the desired device control.

Representative of the types of control systems that may be used with the invention is the microprocessor-based control system described in U.S. Pat. No. 4,940,052 entitled MICROPROCESSOR CONTROLLED RATE-RESPONSIVE PACEMAKER HAVING AUTOMATIC RATE RESPONSE THRESHOLD ADJUSTMENT. Reference is also made to U.S. Pat. Nos. 4,712,555 and 4,944,298, wherein a state machine type of operation for a pacemaker is described; and U.S. Pat. No. 4,788,980, wherein the various timing intervals used within the pacemaker and their inter-relationships are more thoroughly described. The '052, '555, '298, and '980 patents are incorporated herein by reference.

Figure 3:
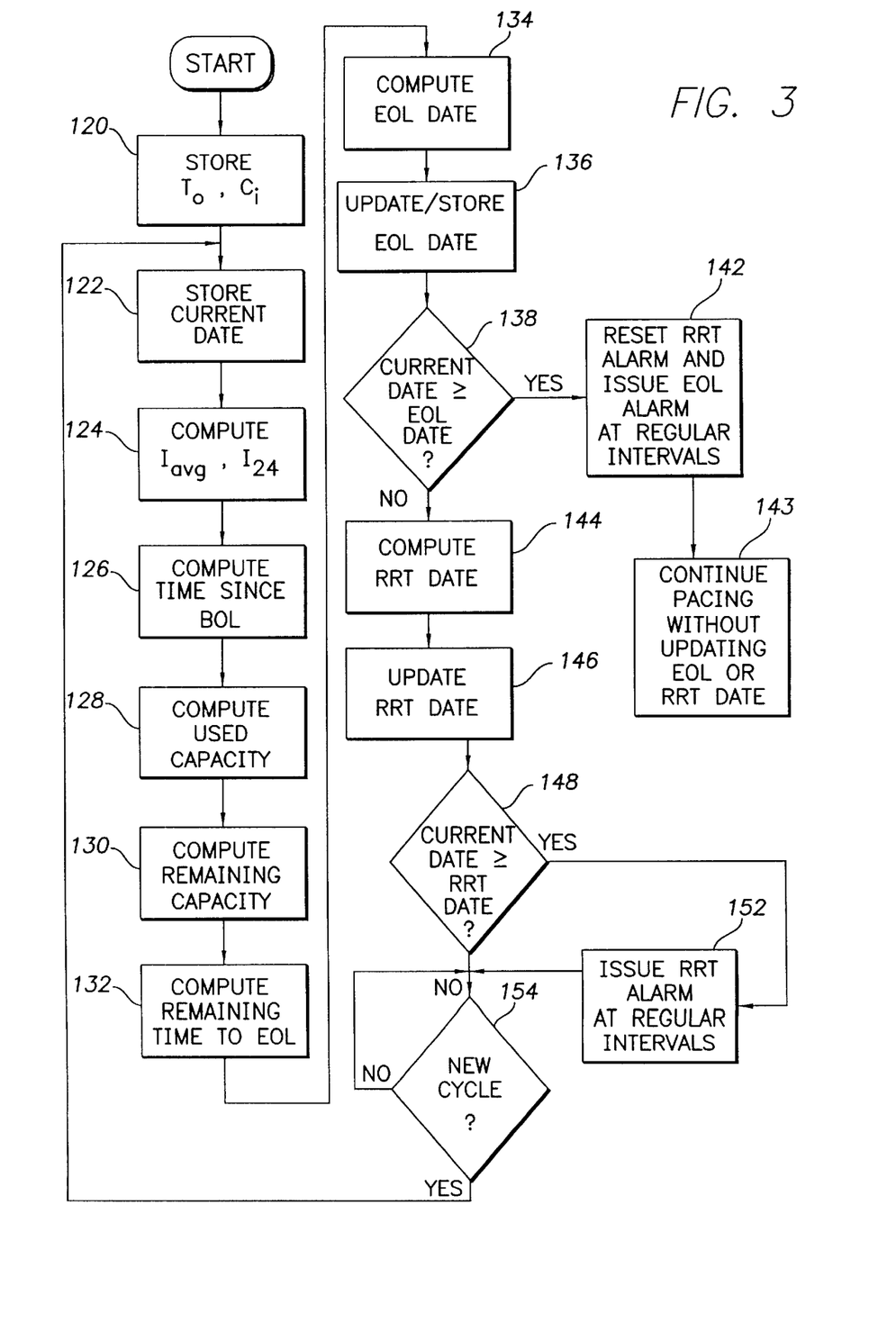
FIG. 3 is a flow diagram illustrating a method of providing precision RRT and EOL indications in accordance with a preferred embodiment of the present invention.

Referring now to FIG. 3, it is a flow diagram which illustrates a method for providing precision RRT and EOL indications in accordance with a preferred embodiment of the present invention. The operative steps illustrated in FIG. 3 may be performed by either the processor 22 of FIG. 1 or the processor 86 of FIG. 2.

The method initiates at a block 120 wherein $T_o$, the battery hook-up date or beginning-of-life (BOL) date, is stored along with $C_i$, the initial energy capacity of the battery. Following block 120, the method advances to block 122 wherein the current date is stored. Next, in block 124, the first current average ($I_{avg}$) and the second current average ($I_{24}$) are determined. The first current average ($I_{AVG}$) keeps track of the average current drawn from the battery since its BOL. The second current average ($I_{24}$) keeps track of the most recent average current, e.g., during the last 24-hour period. As a result, the first current average is an average energy depletion rate since the battery BOL and the second current average is the average energy depletion rate over the last 24-hour period.

The method then advances to block 126 wherein the time since BOL, or the energy depletion time. is determined. Block 126 is performed by subtracting the current date set in block 122 from the battery hook-up date set in step 120. The process then advances to block 128 wherein the actual used energy capacity of the battery is determined. Block 128 is preferably performed by multiplying the first current average which, as previously described, is the average battery current since BOL, by the time since BOL determined in step 126. With the used energy capacity of the battery determined in block 128, the process then advances to block 130 wherein the actual remaining energy capacity of the battery is determined. Block 130 is preferably performed by subtracting the used battery energy determined in step 128 from the initial battery capacity set in block 120.

Once the remaining battery energy capacity is determined, the method advances to block 132 wherein the remaining power source life, or remaining time to EOL, is determined. Block 132 is preferably performed by dividing the remaining battery energy capacity determined in block 130 by the second current average which, as previously described, is the average current drawn from the battery over a last 24 hour period. This renders the remaining time to EOL in day units.

Once the remaining time to EOL is determined, the method advances to block 134 wherein the EOL date, the date of power source depletion, is determined. In accordance with this preferred embodiment, block 134 is performed by adding the remaining time to EOL determined in block 132 to the current date originally set in block 122. This provides an EOL date. The EOL date of block 134 is then used to update the EOL date stored in memory in accordance with block 136.

After the EOL date is determined and updated in memory, the method advances to a block 138. Here, it is determined if the current date equals or exceeds the EOL date. If it is, the method advances to block 142 which resets any RRT alarm (which may have been set in block 152, as described below) and issues an EOL alarm at regularly scheduled intervals. The EOL alarm is an alarm which is perceptible and used to advise the patient or physician that the EOL date has arrived. Once the EOL alarm has been triggered, the device will continue pacing without updating the EOL or RRT dates at block 143. The duration of the EOL alarm may be independently controlled, such as by a latch, to maintain the EOL alarm for some preset period of time without effecting the processing illustrated in FIG. 3.

If the current date has not exceeded the EOL date, then the method advances to block 144 wherein the RRT date is determined. In accordance with this preferred embodiment, the RRT date is determined by subtracting a fixed period of time, such as 90 days, from the EOL date determined in step 134. This will provide an RRT date which precedes the EOL date by 90 days, for example. Once the RRT date is determined, it is then updated in memory in accordance with block 146.

Next, the method advances to block 148 where it is determined if the current date equals or exceeds the RRT date. If it does, the process proceeds to block 152 to cause the RRT alarm to issue at regular intervals. The RRT alarm alerts the patient that the RRT date has been reached. Again, the duration of the RRT alarm may be independently controlled, such as by a latch, without disturbing the processing of the method illustrated in FIG. 3.

Once the RRT alarm is issued or if it is determined in block 150 that the EOL alarm has already issued, the method then advances to block 154 which determines if a new cardiac cycle has begun. The method pauses until a new cycle begins at which time the process returns to block 122. Hence, as can be seen herein, the process steps 122 through 154 are repeated each cardiac cycle. Only block 120 is not repeated since block 120 relates to initial battery parameters which do not change over time.

The RRT and EOL alarms may take many different forms. As known in the art, the RRT and EOL alarms may be audible alarms, utilizing different pitches or audible tone sequences to enable discernment between the RRT and EOL alarms. Alternatively, the alarms may be in the form of a vibration caused by a vibrator within the implantable device. Other forms of alarms are also known and may be utilized in practicing the present invention.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac device having a precise indicator of replacement time, comprising:
    a power source having an initial energy capacity;
    pulse generating means for generating stimulation pulses which deplete the energy capacity of the power source;

prediction means for predicting a remaining energy capacity of the power source based on an actual energy used by the pulse generating means; and means for generating an indicator, based upon the actual remaining energy capacity of the power source, corresponding to the replacement time of the power source.

2. The device of claim 1, wherein the prediction means comprises:

means for subtracting the actual used energy from the initial energy capacity to determine the actual remaining energy.

3. The device of claim 2, wherein the device further comprises:

means for determining an energy depletion time of the power source;

means for determining average energy depletion rate over the energy depletion time; and means for determining the actual energy used based upon the average energy depletion and the energy depletion time.

4. The device of claim 1, further comprising:

means for determining average energy depletion rate; and means for determining remaining power source life based upon the remaining energy capacity and the average energy depletion rate.

5. The device of claim 4, wherein:

the remaining power source life is in day units; and the indicator generating means comprises means for determining a date of power source depletion based upon the remaining power source life and a current date, the date of power source depletion being a first indicator.

6. The device of claim 5, wherein the indicator generating means further comprises:

means for dynamically determining a recommended replacement date for replacing the depletable power source based upon the date of power source depletion date and a fixed time period prior to the date of power source depletion, the recommended replacement date being a second indicator.

7. The device of claim 5, further comprising alarm means for issuing a discernable alarm when the current date equals or exceeds the date of power source depletion.

8. The device of claim 6, further comprising alarm means for issuing a discernable alarm when the current date equals or exceeds the recommended replacement date.

9. The device of claim 4, wherein the average energy depletion rate is an average energy depletion rate of at least a previous twenty-four hour period.

10. An implantable cardiac device having an improved means for predicting replacement time, the device comprising:

a power source having an initial energy capacity;

pulse generating means for generating stimulation pulses which deplete the energy capacity of the power source; and a processor programmed to predict the recommended replacement time based on actual energy used, and to generate an indicator when the recommended replacement time has been exceeded.

11. The device of claim 10, wherein the processor is programmed to predict the recommended replacement time by determining actual energy used and to subtract the actual used energy from the initial energy capacity to determine the actual remaining energy capacity.

12. The device of claim 11, wherein the processor is further programmed to determine an energy depletion time of the power source, to determine average energy depletion rate over the energy depletion time, and to determine the actual used energy based upon the average energy depletion and the energy depletion time.

13. The device of claim 10, wherein the processor is further programmed to determine average energy depletion rate and remaining power source life based upon the remaining energy and the average energy depletion rate.

14. The device of claim 10, wherein the processor is further programmed to predict the absolute replacement time, and to generate an indicator when the absolute replacement time has been exceeded.

15. The device of claim 14, wherein the remaining power source life is in day units and wherein the processor is further programmed to determine an absolute replacement date based upon the remaining power source life and a current date, the absolute replacement date being a first indicator.

16. The device of claim 15, wherein the processor is further programmed to determine a recommended replacement date for replacing the depletable power source based upon the date of absolute replacement date and a fixed time period prior to the absolute replacement date, the recommended replacement date being a second indicator.

17. The device of claim 15, further comprising an alarm that issues a discernable alarm when the current date equal or exceeds the absolute replacement date.

18. The device of claim 16, further comprising an alarm that issues a discernable alarm when the current date equal or exceeds the recommended replacement date.

19. The device of claim 13, wherein the average energy depletion rate is an average energy depletion rate of at least a last twenty-four hour period.

20. In an implantable cardiac device having a power source having an initial energy capacity, a method of monitoring energy depletion of the power source, the method comprising the steps of:

dynamically determining one of a recommended replacement time or an absolute replacement time based on an actual remaining energy of the power source; and generating an indicator, based upon the actual remaining energy of the power source, corresponding to one of a recommended replacement time or an absolute replacement time.

21. The method of claim 20, further comprising the step of determining the actual remaining energy based on determining actual used energy and subtracting the actual used energy from the initial energy capacity.

22. The method of claim 21, wherein the step of determining actual used energy comprises the steps of determining an energy depletion time of the power source, determining average energy depletion rate over the energy depletion time, and multiplying the average energy depletion rate by the energy depletion time.

23. The method of claim 20, further comprising the steps of determining average energy depletion rate, and dividing the remaining energy by the average energy depletion rate to determine remaining power source life.

24. The method of claim 23, wherein the remaining power source life is in day units and wherein the method further comprises the step of adding the remaining power source life to a current date to determine a date of power source depletion as a first indicator.

25. The method of claim 24, comprising the further step of subtracting a fixed time from the date of power source depletion to determine a recommended replacement date as a second indicator.

26. The method of claim 24, comprising the further step of issuing a discernable alarm when the date of power source depletion is a current date.

27. The method of claim 25, comprising the further step of issuing a discernable alarm when the recommended replacement date is a current date.

28. The device of claim 25, wherein the average energy depletion rate is an average energy depletion rate of a last twenty-four hour period.

29. A method for determining a time remaining to a recommended replacement time of a battery of an implantable cardiac stimulating device, comprising:
   determining a first amount of battery capacity actually depleted as a function of an actual battery current used over a depletion time interval;
   defining a second amount of battery capacity corresponding to recommended replacement time;
   determining an amount of battery capacity remaining until the recommended battery replacement time by subtracting the first amount of battery capacity from the second amount of battery capacity;
   measuring an amount of battery current needed to maintain a present level of therapy; and
   predicting the time remaining to the recommended battery replacement time based on the amount of battery capacity remaining and the amount of battery current needed to maintain the present level of therapy.

30. The method of claim 29, further comprising:
   defining the actual battery current used over a depletion time interval as an average current depletion rate over a time interval between battery attachment and interrogation.

31. The method of claim 29, wherein the measuring step comprises:
   determining a most-recent average current depletion representative of a patient's present level of therapy.

32. The method of claim 31, wherein the most-recent average current depletion is an average current depleted over at least a previous twenty-four hour period.

33. The method of claim 31, wherein:
   the most-recent average current depletion is an average current used over approximately a previous twenty-four hour period; and
   the time remaining is calculated in day-units.

34. An implantable cardiac device that determines a time remaining to a replacement time of a battery, comprising:
   a battery current measuring circuit that measures an actual battery current used over a depletion time interval to produce a value for an actual battery capacity depleted, and further measures an amount of battery current needed to maintain a present level of therapy; and
   a memory for storing a total amount of battery capacity corresponding to a battery replacement time, the battery replacement time being one of a recommended replacement time or an end-of-life time;
   a control circuit that determines a remaining amount of battery capacity by subtracting the actual battery capacity depleted from the total amount of battery capacity, the control circuit further predicting the battery replacement time based on the amount of battery capacity remaining and the amount of battery current needed to maintain the present level of therapy.

35. The device of claim 34, wherein:
   the battery current measuring circuit measures the actual battery current used over a depletion time interval by measuring an average current depletion over a time interval between battery attachment and interrogation.

36. The device of claim 34, wherein:
   the battery current measuring circuit measures the amount of battery current needed to maintain a present level of therapy by measuring a most-recent average current depletion representative of a patient's most-recent level of therapy.

37. The device of claim 36, wherein:
   the battery current measuring circuit measures the most-recent average current depletion by measuring an average current depleted over at least a previous twenty-four hour period.

38. The device of claim 36, wherein:
   the battery current measuring circuit measures the most-recent average current depletion by measuring an average current depleted approximately a previous twenty-four hour period; and
   the control circuit predicts the battery replacement time in day-units.

39. An implantable cardiac device that determines a time remaining to a desired replacement time of a battery, comprising:
   measuring means for measuring a value for an actual battery capacity depleted based on an actual battery current and a depletion time interval, and further for measuring an amount of battery current needed to maintain a present level of therapy; and
   storing means for storing a total amount of battery capacity corresponding to the desired replacement time;
   determining means for determining a remaining amount of battery capacity, and for determining the desired replacement time based on the amount of battery capacity remaining and the amount of battery current needed to maintain the present level of therapy.

40. The device of claim 39, wherein:
   the measuring means further comprises means for measuring the actual battery current used over a depletion time interval by measuring an average current depletion over a time interval between battery attachment and interrogation.

41. The device of claim 39, wherein:
   the measuring means further comprises means for measuring the amount of battery current needed to maintain a present level of therapy by measuring a most-recent average current depletion representative of a patient's most-recent level of therapy.

42. The device of claim 41, wherein:
   the determining means further comprises means for determining the battery replacement time in day-units.

43. In an implantable cardiac device having a battery which has an initial energy capacity, a method of determining a replacement time, the method comprising:
   dynamically determining the replacement time based on actual total energy capacity used and predicted future use based on recent energy capacity usage; and
   reporting one of a replacement time or a replacement date whenever interrogation occurs after a battery is connected and until battery end-of-life.

44. The method of claim 43, further comprising:
   measuring a long-term average and a short-term average of the actual battery current used; and wherein the long-term average battery current is used to calculate the actual total energy capacity used and the short-term average battery current is used to predict future use.

45. An implantable cardiac device having a battery which has an initial energy capacity for determining a replacement time, comprising:

control circuitry that is programmed to dynamically determine the replacement time based on actual total energy capacity used and predicted future use based on recent energy capacity usage; and telemetry circuitry that is capable of transmitting one of a replacement time or a replacement date whenever interrogation occurs after a battery is connected and until battery end-of-life.

46. The method of claim 45, further comprising:

measurement circuitry that measures a long-term average and a short-term average of the actual battery current used; and wherein the long-term average battery current is used to calculate the actual total energy capacity used and the short-term average battery current is used to predict future use.

47. An implantable cardiac device having a battery which has an initial energy capacity, comprising:

means for determining actual total energy capacity used;

means for determining a predicted future use based on recent energy capacity usage;

means for dynamically determining the replacement time based on actual total energy capacity used and predicted future use based on recent energy capacity usage; and means for reporting one of a desired replacement time or a desired replacement date whenever interrogation occurs after a battery is connected and until battery end-of-life.

48. The method of claim 47, further comprising:

measurement circuitry that measures a long-term average and a short-term average of the actual battery current used; and wherein the long-term average battery current is used to calculate the actual total energy capacity used and the short-term average battery current is used to predict future use.

49. A method for determining a time remaining to a desired replacement time of a battery of an implantable cardiac stimulating device, comprising:

determining a first amount of battery capacity actually depleted as a function of an actual battery current used over a depletion time interval;

defining a second amount of battery capacity corresponding to a desired replacement time; and determining an amount of actual battery capacity remaining until the desired battery replacement time by subtracting the first amount of battery capacity from the second amount of battery capacity, determining the desired battery replacement time based on the actual amount of battery capacity remaining.

50. A system for determining a time remaining to a desired replacement time of a battery of an implantable cardiac stimulating device, comprising:

a current monitoring circuit that monitors a first amount of battery capacity actually depleted as a function of an actual battery current used over a depletion time interval, and further monitors a remaining battery capacity based on the difference between the first amount of battery capacity and a second amount of battery capacity that corresponds to desired replacement time; and a control circuit that is operative to determine a time for the desired replacement of the device based on the remaining battery capacity.

51. A system for determining a time remaining to a desired replacement time of a battery of an implantable cardiac stimulating device, the battery having a predetermined amount of battery capacity corresponding to a desired replacement time, the system comprising:

means for determining an amount of actual battery capacity remaining based on the difference between the predetermined amount of battery capacity and a first amount of battery capacity actually depleted corresponding to an actual battery current used over a depletion time interval;

determining the desired battery replacement time based on the actual amount of battery capacity remaining.

* * * * *